United States Patent
Jastrzebski et al.

(10) Patent No.: US 6,569,691 B1
(45) Date of Patent: *May 27, 2003

(54) MEASUREMENT OF DIFFERENT MOBILE ION CONCENTRATIONS IN THE OXIDE LAYER OF A SEMICONDUCTOR WAFER

(75) Inventors: Lubomir L. Jastrzebski, Clearwater, FL (US); Alexander Savtchouk, Tampa, FL (US); Marshall D. Wilson, Tampa, FL (US)

(73) Assignee: Semiconductor Diagnostics, Inc., Tampa, FL (US)

( * ) Notice: Subject to any disclaimer, the term of this patent is extended or adjusted under 35 U.S.C. 154(b) by 190 days.

This patent is subject to a terminal disclaimer.

(21) Appl. No.: 09/713,617

(22) Filed: Nov. 15, 2000

Related U.S. Application Data

(63) Continuation-in-part of application No. 09/538,080, filed on Mar. 29, 2000, now abandoned.

(51) Int. Cl.[7] .............................................. H01L 21/66
(52) U.S. Cl. .......................... 438/14; 438/516; 438/545; 438/17
(58) Field of Search ................................ 438/510–569, 438/70–75, 17, 14–16

(56) References Cited

PUBLICATIONS

McBrayer et al., "Diffusion of Metals in Silicon Dioxide", *J. Electrochem. Soc.: Solid–State Science and Technology*, 133:1242–1246, Jun., 1986.
Shacham–Diamand et al., "Copper Transport in Thermal $SiO_2$", *J. Electrochem. Soc.*, 140:2427–2432, Aug., 1993.
Wang, "Barriers Against Copper Diffusion into Silicon and Draft Through Silicon Dioxide", *MRS Bulletin*, pp. 30–40, Aug., 1994.
Vogt et al., "Barrier behaviour of plasma deposited silicon oxide and nitride against Cu diffusion", *Applied Surface Science*, 91:303–307, 1995.

*Primary Examiner*—Matthew Smith
*Assistant Examiner*—Calvin Lee
(74) *Attorney, Agent, or Firm*—Fish & Richardson P.C.

(57) ABSTRACT

A method and apparatus for measuring the concentration of different mobile ions in the oxide layer of a semiconductor wafer from the contact potential shift caused by different ions drifting across the oxide that includes depositing charge (e.g., using a corona discharge device) on the surface of the oxide and heating the wafer to allow different mobile ions in the oxide to drift. The difference in the contact potential measured before and after heating provides an indication of the different mobile ion concentration in the oxide layer.

35 Claims, 12 Drawing Sheets

MEASUREMENT OF DIFFERENT MOBILE ION CONCENTRATIONS IN THE OXIDE LAYER OF A SEMICONDUCTOR WAFER

This application is a continuation-in-part of U.S. Ser. No. 09/538,080, filed Mar. 29, 2000, and abandoned.

BACKGROUND

The invention relates to semiconductor wafer testing.

Mobile ion contaminants within a silicon dioxide ($SiO_2$) oxide layer disposed over a silicon semiconductor wafer can cause problems in the manufacture and performance of integrated circuits. For example, copper metal deposited on the oxide surface to enhance circuit performance can penetrate into the oxide layer during high temperature annealing (400° C. to 500° C.) processes used during IC manufacturing. During prolong circuit operation, copper present in the oxide reduces the oxide layer's resistivity, which increases leakage through the oxide layer and degrades overall circuit performance. Other ionic impurities such as $Na^+$, $Li^+$, and $K^+$ also can be introduced within the oxide layer during high temperature processing. The most common technique for measuring the total concentration of mobile ions in the oxide layer include the capacitance-voltage (CV) method and the triangular voltage sweep (TVS) method. These methods are described in D. K. Schroder, *Semiconductor Material and Device Characterization*, John Wiley & Sons, Inc. (1990), pp. 263–267, hereby incorporated by reference.

Generally, these methods include preparing metal oxide semiconductors (MOS) capacitor patterns on test wafers and applying a voltage to a metal while heating the wafer to move the ions. In the CV methods, the total mobile ion concentration is determined from the differences in capacitance-voltage characteristics caused by a drift of ions; and specifically by the shift in so-called "flat band voltage". In the TVS method, the total mobile ion concentration is determined from the electric current component due to mobile ion drift across the oxide.

SUMMARY

This invention relates to a non-contact, non-destructive method to determine different mobile ion concentrations directly from a change in the contact potential value caused by differential mobile ion redistribution toward or away from the top of the oxide surface.

In one aspect, the invention features a method of measuring at least two different ion concentrations within an oxide layer of a semiconductor. The method includes applying a first predetermined BTS-conditioning to the semiconductor wafer including the oxide layer disposed thereon to cause ions of a first type to migrate within the oxide layer; and applying a second predetermined BTS-conditioning to the semiconductor wafer to cause ions of a second type to migrate within the oxide layer. The first predetermined BTS-conditioning does not substantially cause the ions of the second type to migrate within the oxide layer.

Embodiments of this aspect may include one or more of the following features. The method further includes measuring the first contact potential before and after the ions of the first type migrate within the oxide layer and measuring the second contact potential before and after the ions of the second type migrate within the oxide layer. The method includes a pre-BTS conditioning to cause a random distribution of ions of the first and second types to move into a non-random distribution such as migrating to the surface of the oxide layer or the $Si/SiO_2$ interface. The method includes measuring the oxide leakage current at the first and the second predetermined BTS-conditionings, correcting the first contact potential with the oxide leakage current measured at the first predetermined BTS-conditioning, and correcting the second contact potential with the oxide leakage current measured at the second predetermined BTS-conditioning.

The first and second predetermined BTS-conditionings each include biasing the semiconductor wafer with a predetermined charge from a corona charging element and heating the semiconductor wafer to a predetermined temperature for a predetermined time period. The first and second charges, temperatures, and time durations can be the same or different. The first and the second temperatures each are between about 150° C. and about 300° C.; the first and the second charges each are between about 0.1 to about 6 MV/cm; and the first and the second time periods each are between 30 sec and 3600 sec. The first predetermined BTS-conditioning includes biasing the semiconductor with a charge of about 0.5 MV/cm and heating the semiconductor to about 170° C. for a time period of at least about 2 minutes for a 1000 Å oxide thickness. The second predetermined BTS-conditioning includes biasing the semiconductor with a charge of about 1.5 MV/cm and heating the semiconductor to about 170° C. for a time period of at least about 20 minutes or biasing the semiconductor with a charge of about 1.5 MV/cm and heating the semiconductor to about 225° C. for a time period of at least about 3.5 minutes for a 1000 Å oxide thickness. The ions of the first type, such as Na+, have an ion mobility that is larger than the ion mobility of the ions of the second type, such as Cu+, at a constant temperature. The semiconductor wafer can include a metal layer, such as copper, periodically patterned on a top surface of the oxide layer.

In another aspect, the invention features a method for determining different mobile ion concentrations within an oxide layer disposed on a surface of a semiconductor wafer including depositing a first charge on at least a portion of the surface of the oxide layer at a low temperature at which a first mobile ion does not substantially move, measuring the contact potential on the surface of the oxide layer, heating the semiconductor wafer and oxide layer to a first temperature sufficient to force substantially all of the first mobile ions to migrate across the oxide layer, measuring a first shift in contact potential after said heating to the first temperature, determining the first mobile ion concentration within the oxide layer on the basis of the first shift; depositing a second charge on at least a portion of the surface of the oxide layer at a low temperature at which a second mobile ion does not substantially move, measuring the contact potential on the surface of the oxide layer, heating the semiconductor wafer and oxide layer to a second temperature sufficient to force substantially all of the second mobile ions to migrate across the oxide layer, measuring a second shift in contact potential after said heating to the second temperature, and determining the second mobile ion concentration within the oxide layer on the basis of the second shift. The method can further include determining the oxide leakage current at the first charge and the second charge using the oxide leakage at the first charge and the second charge to determine the first and second ion concentrations.

In another aspect, the invention features a system for the measurement of mobile contaminant ion concentration in an oxide layer of a semiconductor wafer. The system includes a charge deposition device configured to deposit charge on the oxide layer of the wafer; a temperature stress device including a element for heating the wafer to a temperature sufficient to allow mobile ions to drift; a measurement device configured to measure the contact potential; and a semiconductor wafer holder including at least one semiconducting wafer having an oxide layer disposed on a surface of a semiconductor wafer. The oxide layer includes a metal layer patterned onto its surface.

Embodiments may include one or more of the following advantages. The system provides a fast, accurate, and reliable technique for measuring the concentration of different types of mobile ions within the oxide layer of a semiconductor wafer. The technique is non-destructive and during the entire cycle the wafer is contacted only from the back side for the purpose of holding, moving, heating, and cooling the wafer. Thus, the wafer can be characterized without having to sacrifice a portion of the wafer. Moreover, because the technique can be performed relatively quickly, the concentration of different mobile ions can be mapped on the entire region (with the exception of the uncharged reference region) rather than in only particular points on the wafer. The technique makes possible the scanning or mapping of the different mobile ion distribution over the entire wafer surface in a realistic time, e.g., about 10 to 30 minutes for an 8 inch diameter size wafer.

Further features, aspects, and advantages, follow.

DESCRIPTION OF THE PREFERRED EMBODIMENTS

Figure 1:
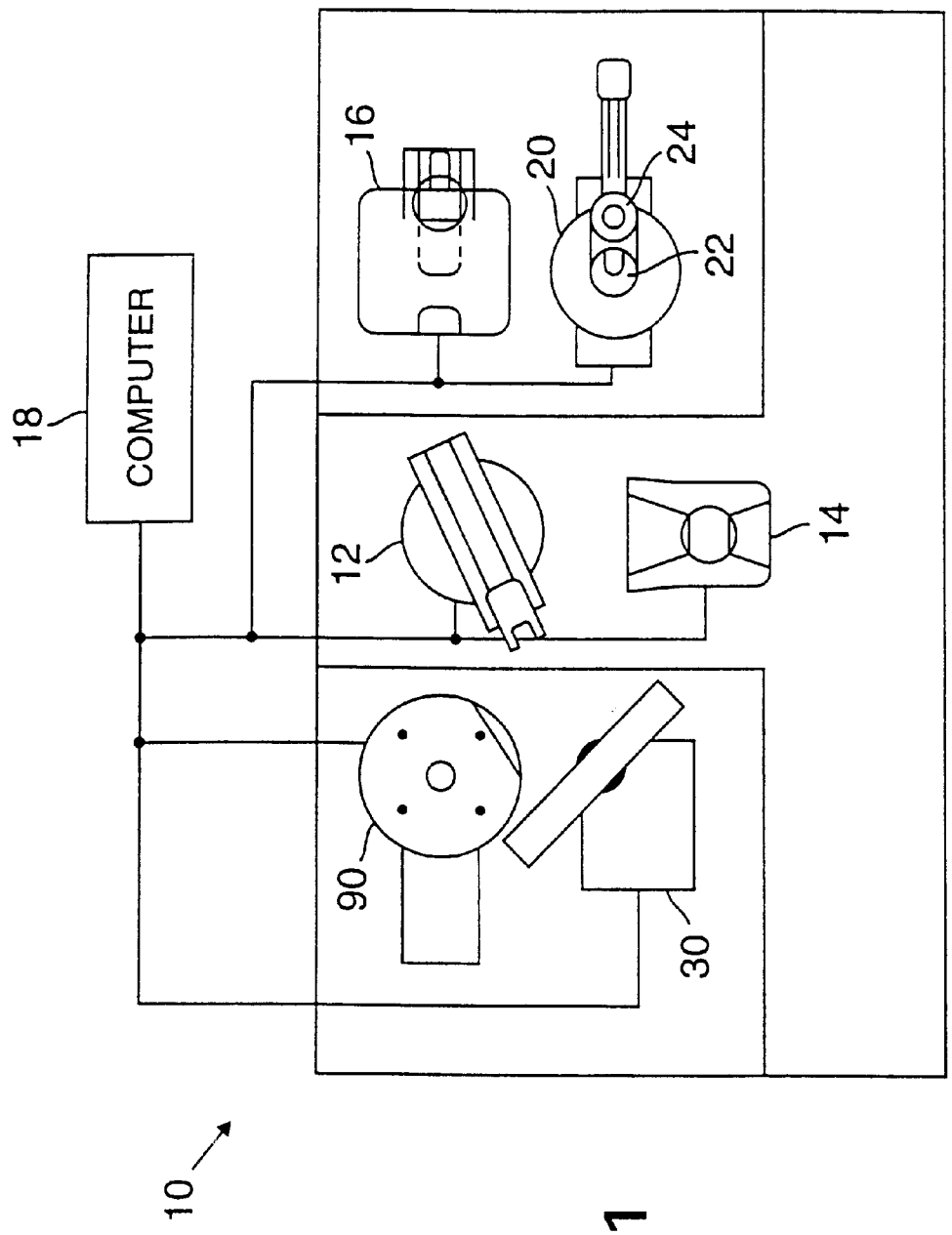
FIG. 1 is a plan view of a measurement system according to the invention.

Referring to FIG. 1, a computer controlled test system 10 for measuring concentrations as of different mobile ions in an oxide layer deposited over a semiconductor wafer is shown. As will be described in conjunction with FIGS. 4A and 4B below, the semiconductor wafer is the type having a $SiO_2$ layer deposited over a semiconductor substrate (e.g., silicon). Test system 10 includes a charge measurement station 20, a corona charging station 30, a temperature stress station 90, a prealigner station 16, and a robotic wafer handler 12 for moving the wafer about the stations of the system.

Charge measurement station 20 also includes a photovoltage transducer probe 24 for measuring the semiconductor surface potential of the wafer. As will be described in greater detail below, the semiconductor surface potential barrier can be used to detect a charging process interfering with the mobile charge concentration determination. A suitable probe and measurement of surface photovoltage is described in Lagowski U.S. Pat. No. 5,177,351 and in Lagowski, "Determining Long Minority Carrier Diffusion Length", U.S. Ser. No. 08/312119, filed Aug. 26, 1994, the entire contents of which are incorporated herein by reference. A suitable device and method are also described in: P. Edelman, J. Lagowski, L. Jastrzebski, "Surface Charge Imaging in Semiconductor Wafers by Surface Photovoltage (SPV)" MRS Symposium Proceedings, 261, pp. 223 (1992), the entire contents of which are incorporated by reference.

Figure 2:
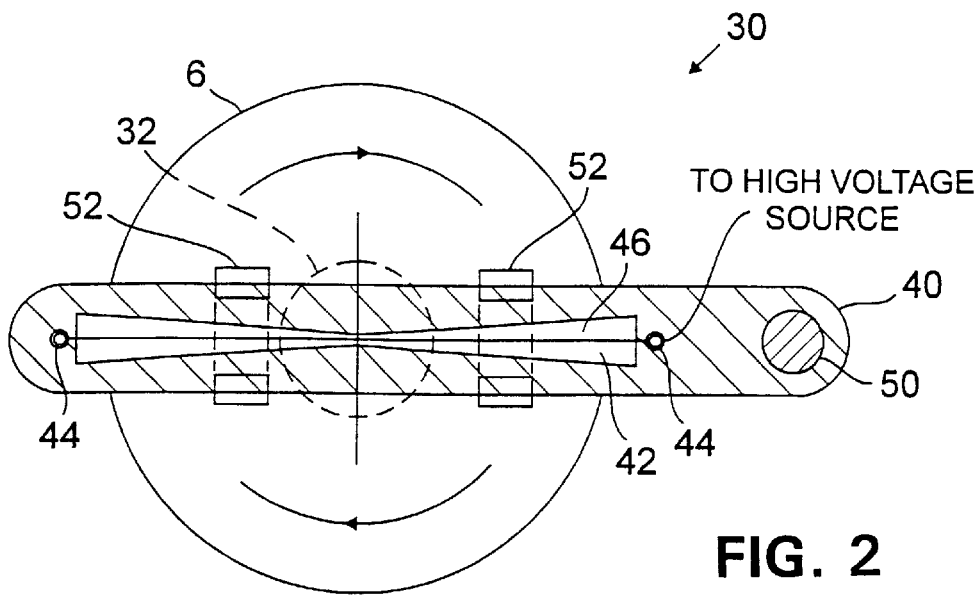
FIG. 2 is a top view of a corona discharge device of the measurement system of FIG. 1.
Figure 3:
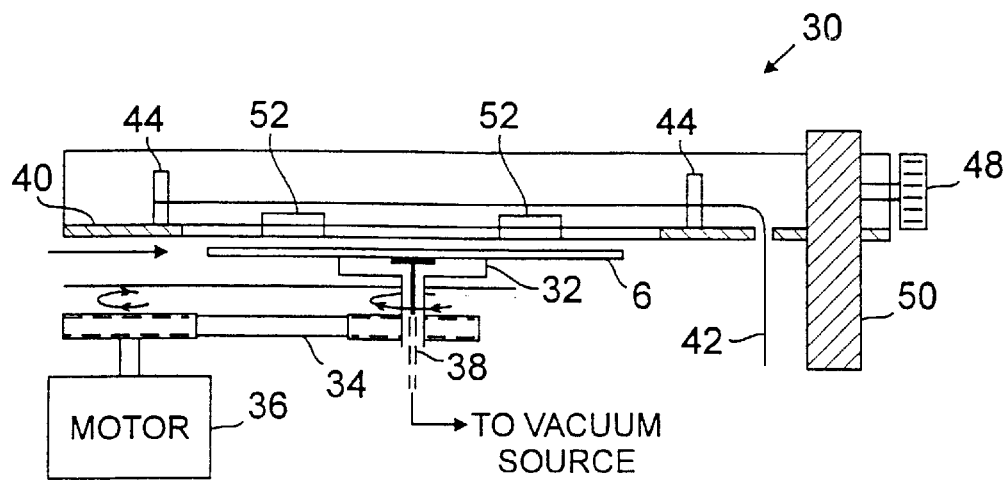
FIG. 3 is a side view of the corona discharge device of the measurement system of FIG. 1.

Referring as well to FIGS. 2 and 3, the corona discharge device 30 deposits charge on the oxide layer surface of the wafer. Corona charging station 30 includes a wafer chuck 32 which is rotated via a belt 34 connected to a motor 36. Wafer 6 is held securely in place on wafer chuck 32 by vacuum provided from an external vacuum source (not shown) and through an aperture 38 passing through wafer chuck 32. An aluminum plate 40 is positioned between 2–3 mm above wafer 6 and serves as a ground terminal for a discharge wire 42 connected to a high voltage source (not shown). Wire 42 extends across the wafer between a pair of teflon posts 44 mounted on plate 40. Plate 40 includes a slotted aperture 46 wider at its ends and narrower at its center so that when the wafer is rotated, deposition of charge emitted from wire 42 through aperture 46 and onto wafer 6 is substantially uniform. The spacing of the wafer from plate 40 with respect to wafer 6 is adjusted by rotating knob 48 on mounting post 50. The dimensions of aperture 46 and spacing between plate 40 and wafer 6 are both determined empirically to provide the desired level and uniformity of charge on the wafer. For effective mobile ion drift at temperatures of about 165–30° C., the electric field in the oxide should be typically $5 \times 10^5$ V/cm or higher. Such a field can be achieved by deposition of a charge of about $10^{12}$ ions/cm². In the corona charging device, the charge deposited is controlled by the charging time and the wafer rotation speed. The quantitative corona charging characteristics, e.g. the charge versus time and the charge versus rotation speed are determined empirically and are introduced into computer software, controlling the corona charging station.

Masking plates 52, fabricated of metal, are positioned across aperture 46 of plate 40 an equal distance from the center of the aperture to prevent deposition of charge over a ringed-shaped portion of the wafer. As will be discussed below, this ringed-shaped portion establishes a reference region 82 (FIG. 10) used in distinguishing between mobile ion drift and other effects of temperature stress on contact potential measurements.

Referring again to FIG. 1, system 10 also includes temperature stress station 90, for heating the wafer after depositing the charge, which contains two temperature-controlled wafer chucks. A heating chuck is provided by an electric heating plate for heating the wafer to a pre-selected temperature from e.g., 165–300° C. A cooling chuck is provided by a water (or air) cooled aluminum plate which cools the wafer, e.g., to room temperature. Both heating and cooling chucks hold the wafer by means of a vacuum suction which assures good thermal contact. The chucks are placed one above the other (with a heating chuck on the top) and transport of the wafer from heating to cooling chuck is done by the robotic handler 12.

Test system 10 further includes a wafer cassette holder 14 for storing the semiconductor wafers to be tested and a prealigning stage 16 for accurate positioning of the wafer as it is moved from device to device, thereby minimizing positioning errors from measurement to measurement. The prealigner station 16 is used for pre-orientation of the wafer prior to measurement by using a notch or flat made by wafer manufacturers near the edge of the circular wafer for exactly that purpose. A computer 18 controls robotic wafer handler 12 and transmits controls signals to and receives data signals from cassette holder 14, charge measurement station 20, corona discharge device 30, and temperature stress station 90.

Figure 4A:
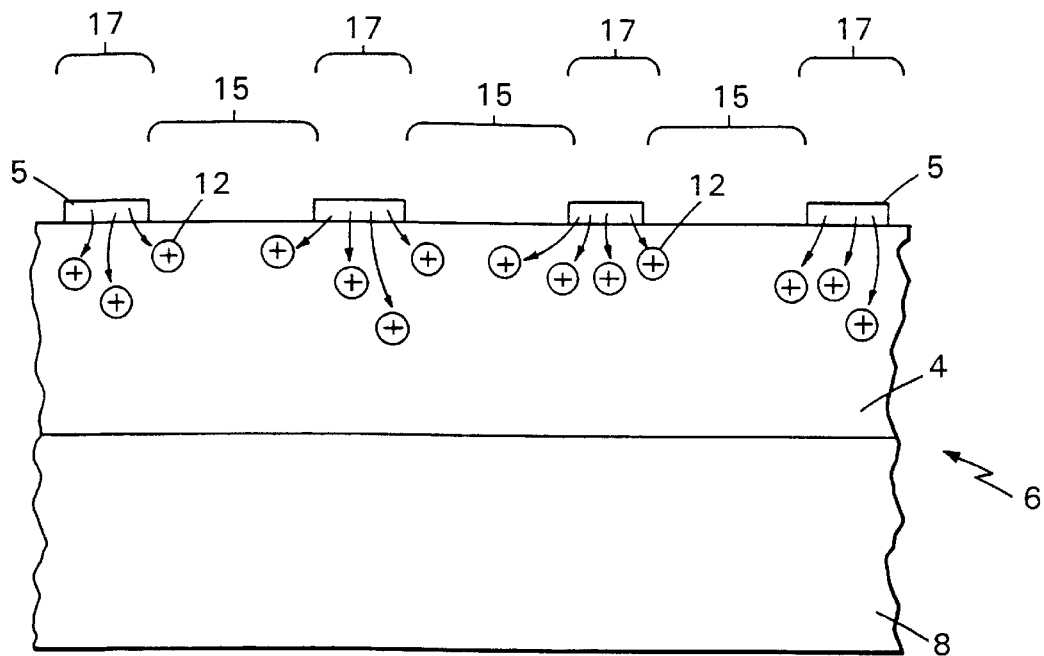
FIG. 4A is a side view schematic of a semiconductor wafer including a metal layer patterned onto the oxide layer.

Referring to FIG. 4A, wafer 6 may be characterized using test system 10 to measure different concentrations of mobile ions. Wafer 6 includes an oxide layer 4, such as $SiO_2$, disposed over a semiconductor layer 8, such as silicon. In order to increase circuitry speeds, a metal layer 5, e.g., copper, is periodically deposited on the surface of oxide layer 4. Typically, a barrier layer (not shown), such as TaN, is disposed between metal layer 5 and oxide layer 4 to prevent penetration of the metal layer into the oxide layer. When semiconductor wafer 6 is heated to high temperatures, such as 400° C., failure of the barrier layer could cause some metal atoms to leach into oxide layer 4 as ions 12. As discussed above, metal ions 12 in oxide layer 4 can degrade overall circuit performance of devices made with semiconductor wafer 6. As a result, it is necessary to measure the concentration of metal ions 12 in oxide layer 4 prior to forming devices to ascertain whether or not oxide layer 4 contains acceptable levels of metal ions. Acceptable levels of ion contaminants depend upon the specific devices being produced and the required circuitry tolerances. Once tested, semiconductor wafers including too high of a concentration of metal ions can be disregarded and those having acceptable levels of ion contaminants can be further processed.

As will be described in more detail below, system 10 applies both a biasing charge and increased temperature to semiconductor wafer 6 and measures the contact potential of the semiconductor in regions 15 devoid of metal layer 5 to quantify the concentration of metal ions 12 in oxide layer 4. The concentration of metal ions 12 in regions 15 is not an absolute measure of the concentration of ions present in regions 17, i.e., those regions directly beneath metal layer 5 and the barrier layer, if present. System 10 establishes a relationship between the concentration of ions measured in regions 15 to the concentration of ions in region 17 by performing measurements on a calibration semiconductor wafer.

Figure 4B:
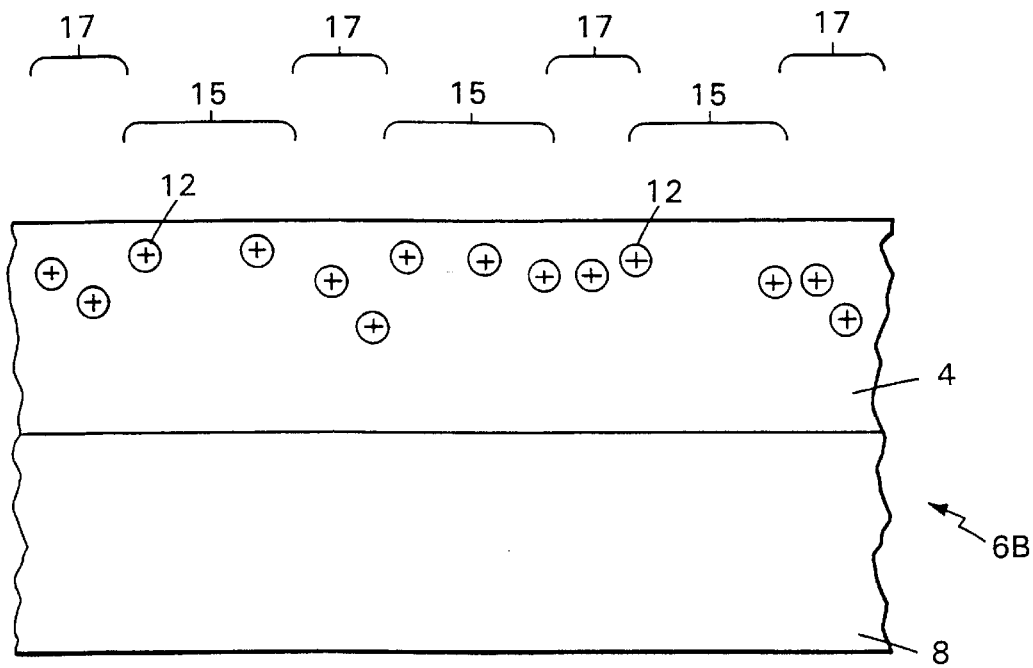
FIG. 4B is a side view schematic of the semiconductor wafer of FIG. 4A with the metal layer removed.
Figure 5A:
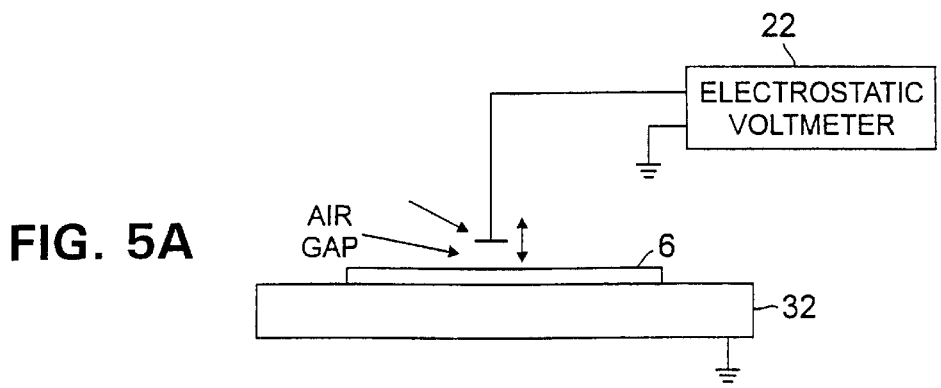
FIG. 5A is a side view schematic of a semiconductor wafer during contact potential measurement.
Figure 5B:
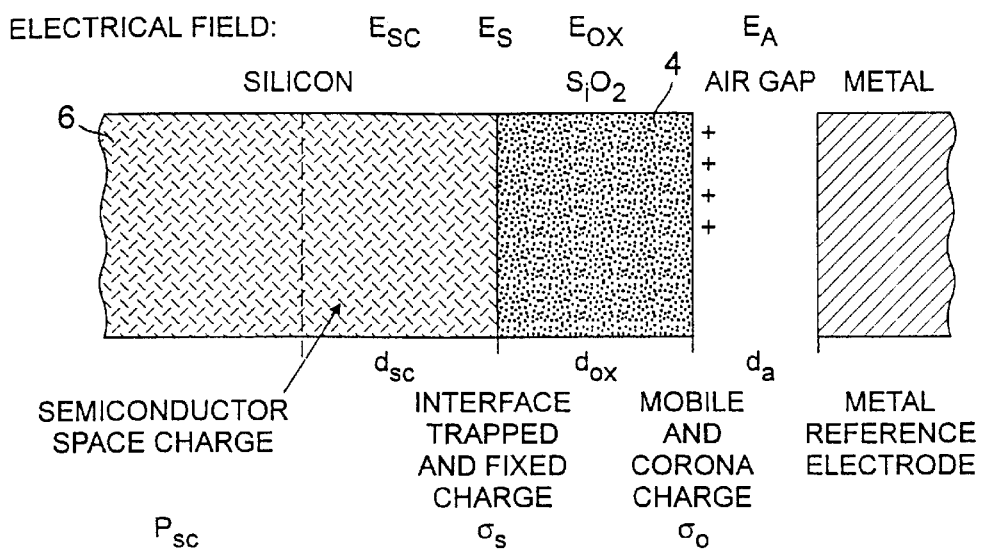
FIG. 5B is a cross sectional view of a semiconductor wafer having an oxide layer separated from a reference electrode by an air gap.
Figure 5C:
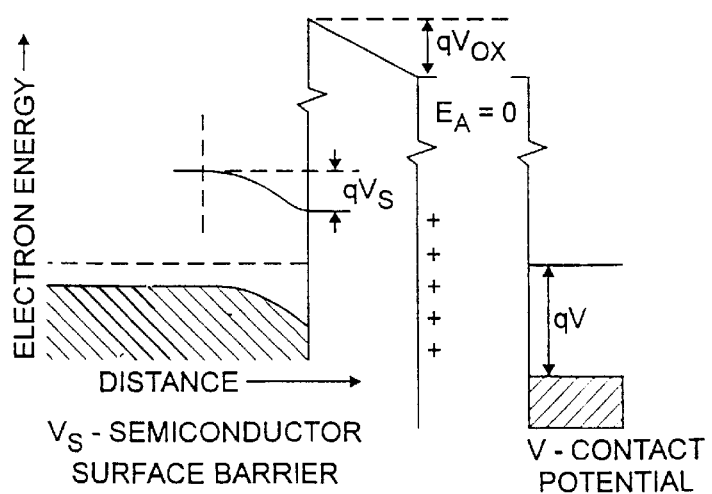
FIG. 5C is an energy band diagram corresponding to FIG. 5B.

Referring to FIG. 4B, a calibration semiconductor 6b is the same wafer described in FIG. 4A, except that metal layer 5 and barrier layer, if present, have been removed from oxide layer 4 after the annealing process. In general, the metal and barrier layers can be removed from the semiconductor wafer by any known method such as by a mild acid treatment, i.e., 0.1M hydrofluoric acid or 0.1M hydrosulfuric acid. Once metal layer 5 and the barrier layer, if present, have been removed, the concentration of metal ions present in regions 17 and 15 are separately determined by system 10. System 10 then calculates and stores a relationship between the measured concentrations in the two regions as a function of both the annealing conditions, i.e., temperature and time duration, and the pattern of metal layer 5 fabricated onto dielectric layer 4, i.e., width and thickness. Prior to operating system 10, the user loads metal fabricated and annealed semiconductor wafers 6 into wafer cassette holder 14 and enters the parameters for the annealing and fabricating conditions into computer 18 which, in turn, loads the appropriate concentration relationship into memory. During ion measurement of regions 15, system 10 uses the relationship stored within memory to determine the concentration of ions in regions 17.

Similar calibration procedures will be used when the metal pattern is smaller than the size of the measurement spot such that a plurality of metal lines fall within a single measurement spot, e.g., when the measurement spot size is about 1 mm and the metal lines have a width of about 0.25 microns spaced apart by about 0.5 microns. In this situation, measurements are first performed on the sample with the metal lines. Then the metal structure is removed and the measurements are repeated. The system 10 stores the relationship between the first and second measurement and computes the ratio of these measurements. System 10 uses the ratio as a calibration factor for all measurements done on the wafer having the specified pattern of metallic lines. This calibration method can also be repeated for different metallic line patterns to establish calibration factors for several metallic line patterns. System 10 stores a plurality of calibration factors, each factor for a specific metallic line pattern, which are used to determine the mobile ion concentration. During operation, the user identifies the metallic line pattern on the wafer so that system 10 recalls the corresponding calibration factor for computing the mobile ion concentration.

Measurement of Mobile Ions

Referring as well to FIGS. 5A–5C, 6A–6C, and 7A–7C, the system measures mobile ion concentrations in the oxide layer by measuring the contact potential V and the semiconductor surface potential barrier $V_s$, before and after specific ions are forced to redistribute in the oxide due to drifting in the field created by corona change. The distance and rate at which different ions drift through the oxide layer depends on the mobility, $\mu$, of each ion in the oxide layer and the bias temperature stress (BTS) conditions, i.e., the magnitude of corona charge, temperature, and time duration. The concentration of specific ions within the oxide layer is measured by sequentially redistributing ions via different BTS conditions and calculating the difference between the contact potential, V, and the semiconductor surface potential barrier $V_s$. Ions having the same ion mobility at the same temperature, generally, cannot be separately measured by changing the BTS conditions. Semiconductor wafer 6, having a silicon dioxide layer 4, is shown in a cross-section in FIG. 5B and in FIGS. 6A–6C. As described above, ionic impurities 70, including, but not limited to, copper ($Cu^+$), sodium ($Na^+$), potassium ($K^+$), and lithium ($Li^+$), are introduced into silicon dioxide layer 4 during elevated temperature processing. For the purpose of providing an example, in FIG. 6A $Na^+$ ions are illustrated as initially located near the top of the $SiO_2$ surface. These ionic impurities are immobile at room temperature. In system 10 the charge 72 (in this case, a positive charge), is deposited on the $SiO_2$ surface using the corona discharge device 30. Schematic representation of corresponding changes in silicon $SiO_2$ and of the energy band diagrams are shown in FIGS. 6A–6C and FIGS. 7A–7C.

Figure 7A:
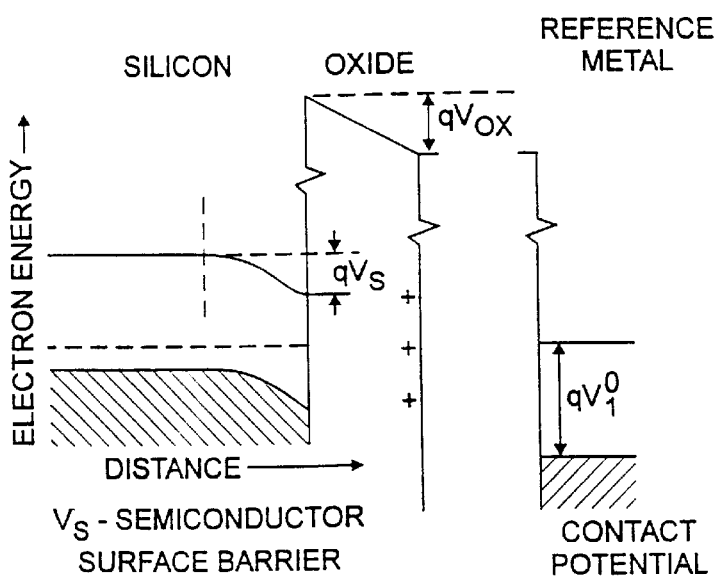
FIGS. 7A–7C are energy band diagrams corresponding to FIGS. 6A–6C respectively.
Figure 7B:
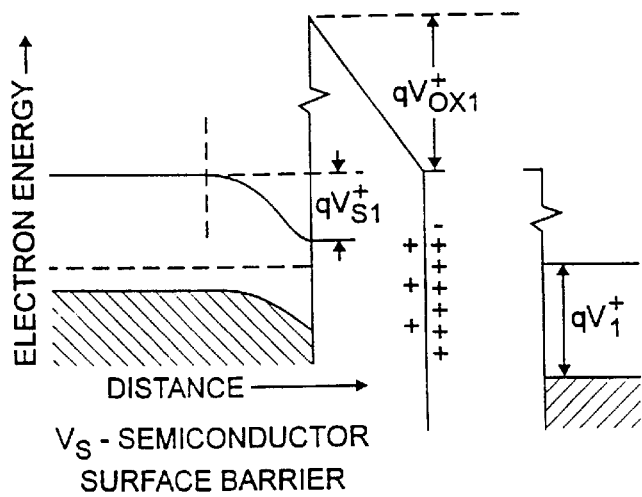
Figure 7C:
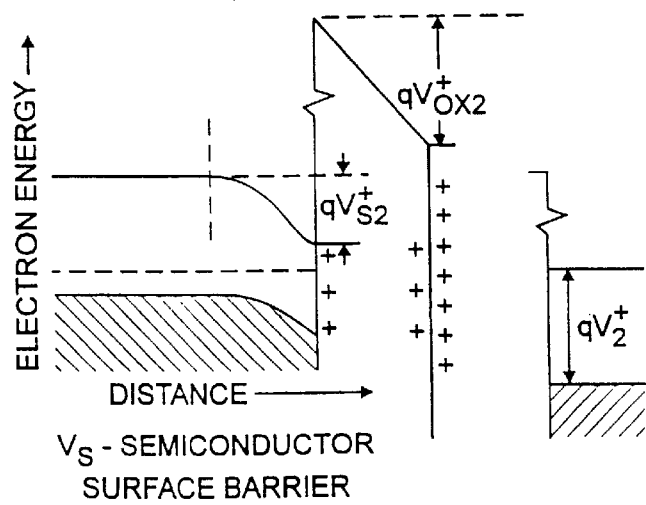

Referring particularly to FIGS. 7A–7C, the charge 72 changes two quantities: the value of the semiconductor surface barrier $V_s$ and the value of the potential drop across the oxide $V_{ox}^+$. The change of $V_s$ is typically only a fraction of a volt. The change of $V_{ox}$ may be a fraction of a volt for a thin, e.g., 100 Å thick oxide, or by many volts for thicker oxides. The term $\Delta V_{ox} \cong \sigma_c \Box d_{ox}/K_{ox} \in_0$, where $\sigma_c$ is the corona charge per cm$^2$, $d_{ox}$ is the oxide thickness, $K_{ox}$ is the dielectric constant of SiO$_2$ and $\in_0$ is the permittivity of free space.

As illustrated in FIGS. 7A and 7B, the contact potential $V_i^+$ change includes contribution due to changes in $V_s$ and changes in $V_{ox}$. Wafer 6 is then heated at temperature stress station 90 to a temperature sufficient to allow the ion impurities 70 to become mobile and move away from the top surface due to electrostatic repulsion by corona charge 72. This corona temperature stress causes a drift of the ionic impurities 70 to the silicon/silicon oxide interface 8 (FIG. 6C). As a result, a potential drop across the oxide decreases to a new value, $V_{ox2}^+$, which is lower than the pre-stress value, $V_{ox1}^+$. In the case of ideal mobile ion drift, the surface potential barrier does not change because its value is determined by the total surface charge (in this case, ionic charge plus corona charge) irrespective of the charge location with the oxide. If $V_{S2}^+ = V_{S1}^+$, then $V_{ox1}^+ - V_{ox2}^+ = V_1^+ - V_2^+$ and the mobile ion concentration can be determined from a difference $V_1^+ - V_2^+$ in the contact potential value measured with sensor 22.

If $V_{S2}^+ \neq V_{S1}^+$ and, especially if a change is significant, then the contact potential change must be corrected for a change in the surface barrier. This may be caused by charge injection from a semiconductor into the oxide during corona temperature stress. Surface barrier corrections will be especially significant for thin oxides, e.g., of the thickness of 100 Å and below, which are used as gate oxides in the most advanced silicon integrated circuits.

Figure 6A:
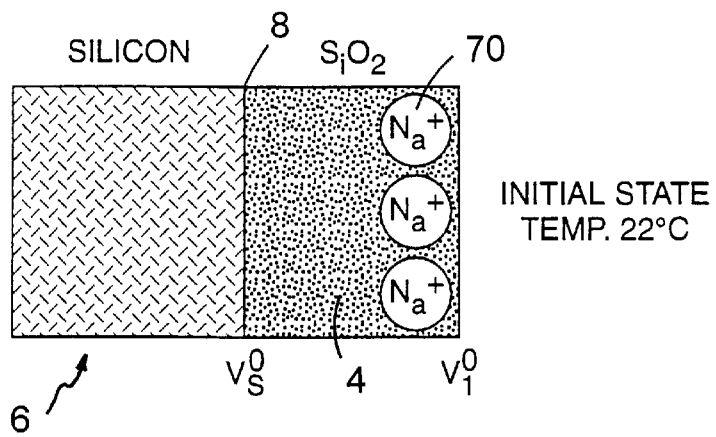
FIGS. 6A–6C are schematic representations of cross-sections of a semiconductor wafer having an oxide layer that illustrate the influence of an electric field on the distribution of mobile ions in the oxide layer.

The simple case of FIG. 6A, where mobile ions are initially located near the top of the SiO$_2$ surface, may not be representative of high temperature processed wafers. Therefore, a more accurate procedure for measuring mobile ion concentration incorporates sequential negative corona temperature stress and positive corona temperature stress. The negative corona temperature stress moves positive mobile ions 70 toward the top of the SiO$_2$ surface. The subsequent positive corona temperature stress is applied for determining the mobile ions concentration (in accordance with FIGS. 6A–6C).

Information on initial distribution of mobile ions can be obtained by comparing the absolute magnitude of contact potential changes after the first negative corona temperature stress with those of the second positive corona temperature stress. Alternatively, a positive corona temperature stress can be used as the first step in the sequence creating ion distribution as shown in FIG. 6C. Then the negative corona temperature stress moves ions to the top of the surface as a second step.

Figure 8A:
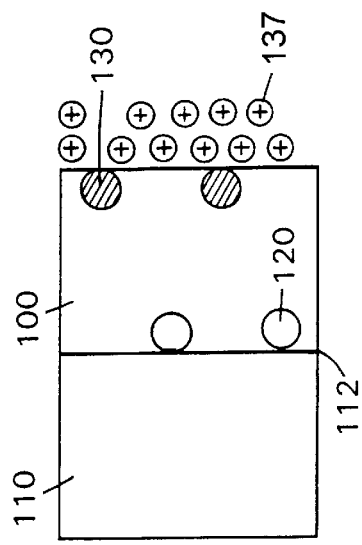
FIGS. 8A–8F are schematic representations of cross-sections of a semiconductor wafer having an oxide layer that illustrate the influence of an electric field on the distribution of two mobile ions in the oxide layer.
Figure 8B:
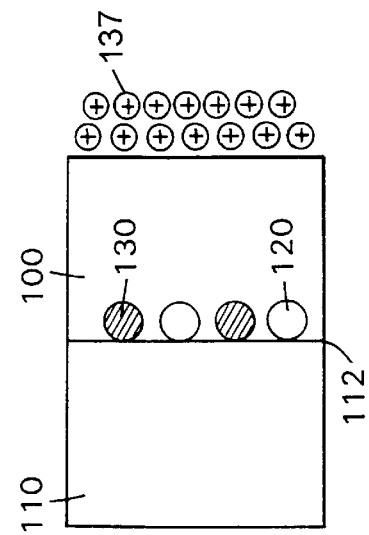
Figure 8C:
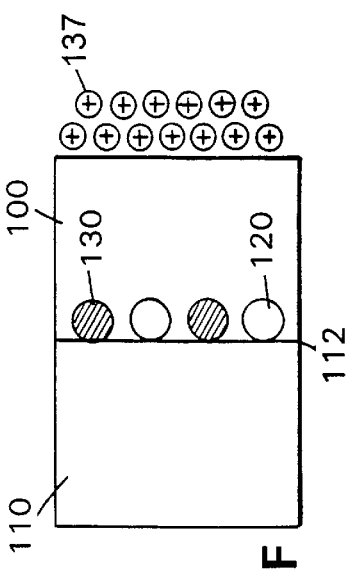
Figure 8D:
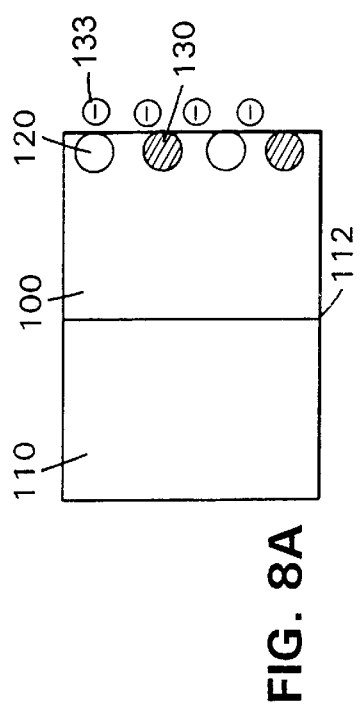
Figure 8E:
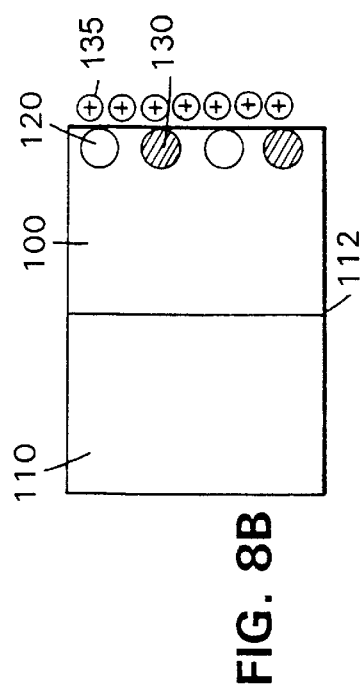
Figure 8F:
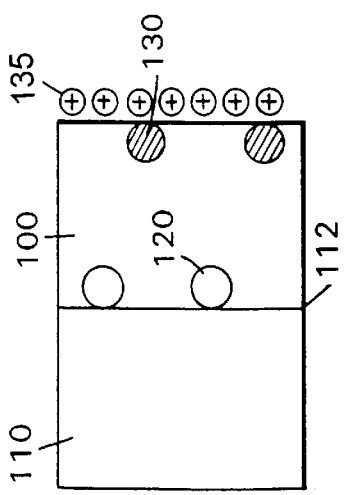

Referring to FIGS. 8A–8F, an oxide layer 100 disposed on a surface of a silicon wafer 110 includes two sets of mobile ions 120 and 130, each set having a different value of ion mobility at the same temperature. For example, ions 120 have a higher mobility relative to ions 130 which implies that milder BTS conditions will affect the migration of ions 120 more than ions 130. The concentration of mobile ions 120 and 130 is determined sequentially and individually by applying in serial fashion BTS conditions to force specific ions away from oxide layer 100 without affecting other ions in oxide layer 100. As discussed above, the BTS conditions are a function of the bias charge applied to the surface of oxide layer 100 as well as the change in temperature and time duration of the biasing charge and temperature change. In operation, system 10: (1) applies a negative corona charge 133 to oxide layer 100; and (2) heats wafer 110 and oxide layer 100 to force all of the mobile ions in oxide layer 100 to the surface (FIG. 8A). System 10 then applies a positive corona charge 135 to the surface of oxide 100 and measures the contact potential of the wafer (FIG. 8B). In general, the magnitude of corona charge 135 is preselected so that ions 120 and 130 do not substantially migrate at room temperature. Next, system 10 applies elevated temperatures for specific time periods to the wafer to force ions 120 towards a Si/SiO$_2$ interface 112 without causing mobile ions 130 to move. System 10, again, measures the contact potential of the wafer (FIG. 8C). As will be discussed in more detail below, the difference in contact potential measured in FIG. 8B and FIG. 8C is proportional to the concentration of mobile ion 120. To determine the concentration of mobile ion 130, system 10 applies a sufficient corona charge 137 to the surface of oxide 100 to move substantially and preferably all ions 130 to interface 112 and measures the contact potential of the wafer (FIG. 8D). System 10 applies elevated temperatures to the wafer for specific time periods to force substantially and preferably all ions 130 to migrate towards interface 112, and then measures the contact potential of the wafer (FIG. 8E). In general, the amount of corona charge deposited on the surface of the wafer to force different ions to migrate, i.e., FIGS. 8B and 8D, can be the same or different. Likewise, the temperature and time duration used by system 10 to force selective migration of different ions can be the same or different. Typically, system 10 changes at least one of the BTS conditions to force selective ion movement. The relationship between corona charge, temperature, and time duration, as well as their effect on ion migration are discussed below.

Theoretical Treatment and Calculations

The phenomena of mobile ion drift under corona temperature stress relates to measured quantities via the equations described in P. Edelman et al., "New Approach to Measuring Oxide Charge and Mobile Ion Concentration", SPIE—The International Society for Optical Engineering, Vol. 2337, pp. 154–164 (1994), incorporated herein as a reference.

The contact potential V in FIG. 5 is:

$$V = V_{ox} + V_s + \text{const.} \quad (1)$$

where $V_{ox}$ is the oxide potential barrier in volts; $V_s$ is the semiconductor surface potential barrier in volts; and const. is the constant depending on the work function of the metal used as a reference electrode in contact potential measurement.

$V_{ox}$ is the quantity which changes due to corona ion deposition and due to mobile ion drift across the oxide layer. $V_{ox}$ can be expressed as:

$$V_{ox} = \frac{q}{K_{ox}\varepsilon_o}\left(\left(\sum_{i=1}^{N}\int_o^{d_{ox}}\rho(Ion)_i x\,dx\right) + [d_{ox} * Q_{corona}]\right) + V_o \quad (2)$$

where: $\rho(Ion)_i$ represents the density of the ith mobile ion in the oxide as a function of distance from Si/SiO$_2$ interface (x); x is the distance of the ion from the interface; $d_{ox}$ is the thickness of the oxide layer; $K_{ox}$ is the dielectric constant of oxide ($K_{ox}=3.9$ for SiO$_2$); $\in_0$ is the permittivity of free space; $V_o$ is the built-in voltage of the oxide due to charged stationary traps; and $Q_{corona}$ is the charge deposited by corona on the oxide surface.

During bias temperature stress, $V_{ox}$ will change due to movement of the mobile ions in the oxide which changes $\rho(Ion)_i$. When all of the ions move to the Si/SiO$_2$ interface, they will no longer contribute to the $V_{ox}$. For movement of only one ion, $V_{ox}$ can be represented by $$V_{ox}=\sigma_c/C_{ox}+\gamma\cdot\sigma_m/C_{ox}+\gamma_1\cdot\sigma_1/C_{ox} \quad (3)$$

where $\sigma_c$ is the corona charge per unit surface area; q is the elemental charge; $\sigma_m$ is the mobile ion surface charge density and is equal to the sum of charge, q, of each ion; $\sigma_1$ is the surface density of other charges in oxide which are immobile; $C_{ox}$ is the oxide capacitance per unit surface area; and $\gamma_1$ is the factor depending on the distribution of charges $\sigma_1$ throughout the oxide. $C_{ox}$ is equal to $K_{ox}\epsilon_0/d_{ox}$; $d_{ox}$ is the oxide thickness. $\gamma_1$ is discussed in D. K. Schroder, Semiconductor Material and Device Characterization; John Wiley & Sons, Inc., 1990; p. 254 the entire contents of which is incorporated by reference. $\gamma=1$ if all ions are near the top surface; $\gamma=0$ if all ions are near silicon/SiO$_2$ interface; and $\gamma=\frac{1}{2}$ when ions are distributed uniformly throughout the oxide thickness.

The ith mobile ion concentration is related to a change in $V_{ox}$ caused by the ith ion drift by:

$$N^i_{ion}=(1/\gamma q)C_{ox}\cdot(\Delta V_{ox}) \quad (4)$$

where $N^i_{ion}$ is the mobile ion concentration per cm$^2$. The corresponding numerical expression for SiO$_2$ is:

$$N^i_{ion}[\text{cm}^{-2}]=(2.15/\gamma)\cdot10^{14}\cdot\Delta V_{ox}/d_{ox} \quad (5)$$

where $\Delta V_{ox}$ is in volts and $d_{ox}$ is in [Å]. $\Delta V_{ox}$ is determined as from the contact potential shift $\Delta V$ as:

$$\Delta V_{ox}=\Delta V-\Delta V_s$$

where $\Delta V_s$ is the difference in semiconductor surface potential barrier. As a result, equation (5) can be rewritten as:

$$N^i_{ion}[\text{cm}^{-2}]=(2.15/\gamma)10^{14}(\Delta V-\Delta V_s)/d_{ox} \quad (6)$$

In general, the BTS conditions are selected such that the ith ion is forced to migrate a distance, d, equal to the thickness of the oxide layer, $d_{ox}$, without forcing the other ions in the oxide to migrate away from the surface of the oxide. Once at the Si/SiO$_2$ interface, the ith ion, typically, does not further penetrate into the silicon wafer. In general, ions forced to the interface are stationary and have no effect on the contact potential measurements associated with subsequent BTS conditioning of the wafer, i.e., those conditions designed to force different ions to migrate from the oxide surface towards the interface. The distance, d, at which the ions migrate within the oxide layer of the silicon wafer is proportional to the relationship:

$$t\cdot E\cdot\mu_i \quad (7)$$

where t is the time duration of the stress conditions; E is the electric field applied to the oxide surface, and $\mu$ is the mobility of the ith ion. Ion mobility is given by $$\mu \propto \frac{q}{kT}\cdot D_o\exp\left(\frac{-qE_a}{kT}\right) \quad (8)$$

in which $D_o$ is the ion diffusivity; k is the Boltzman constant; T is the temperature; $E_a$ is the activation energy; and q is defined above. In general, the mobility of most elemental ions are known. If the mobility of an elemental ion is unknown, it can be determined by performing analytical tests such as secondary ion mass spectroscopy (SIMS) measure how far the ion diffuses into the oxide layer at specific temperatures. SIMS experiments are described, for example, in D. K. Schroder, Semiconductor Material and Device Characterization, John Wiley & Sons, Inc. (1990).

Based on the types of ions and their mobilities in the oxide layer at specific temperatures, a set of BTS conditions can be determined from equation (7) to force each type of ion to migrate a distance equal to the oxide thickness, $d_{ox}$, without substantially affecting the other types of ions at the surface of the oxide layer. The oxide thickness is determined independent of the concentration measurements by known techniques such as SIMS and elipsometry. If the types of ions present in the oxide are unknown, they can be determined by analytical techniques such as atomic absorption spectroscopy.

In general, the BTS conditions, i.e., the biasing charge, time duration, and temperature, are varied to selectively force different types of ions to migrate towards the oxide/semiconductor interface in sequence beginning with the highest mobile ions and ending with the lowest mobile ions. The exact BTS conditions can be fine tuned by cross-checking or calibrating the predicted effects of ion migration, i.e., distance, type of ion effected, and flux of ions migrating towards the interface, against analytic measurements, such as SIMS, conducted on wafers processed under similar BTS conditions. Before operating system 10, the user enters the oxide thickness, the types of ions present in the oxide layer, and their mobilities at specific temperatures. Computer 18 uses this information along with equations (7) and (8) to calculate a sequence of BTS conditions to selectively measure the concentration of each ion type. The user can also program computer 18 to execute the BTS conditions determined from cross-checking or calibrating experiments. In this scenario, the user enters the BTS conditions for each ion and the order in which they should be executed.

Figure 6B:
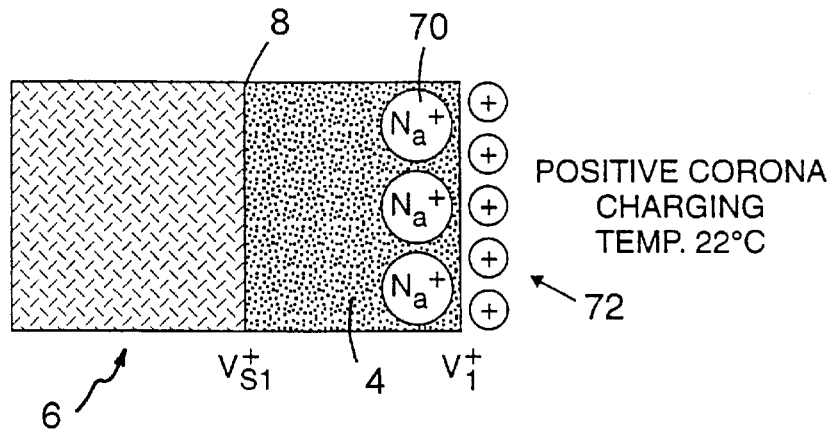
Figure 6C:
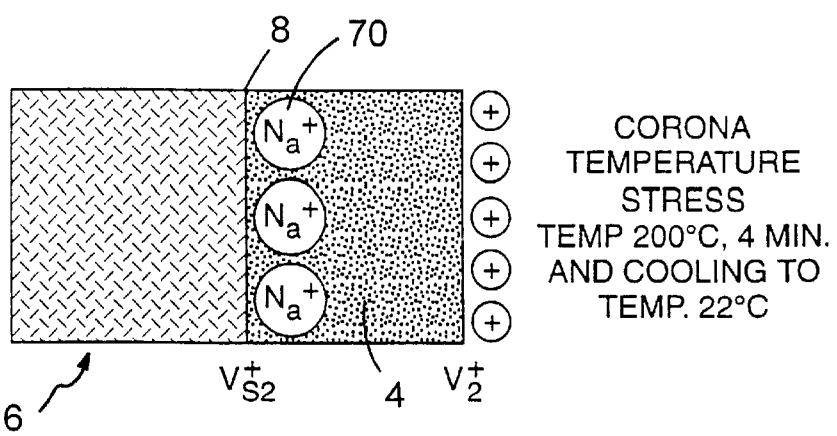
Figure 9:
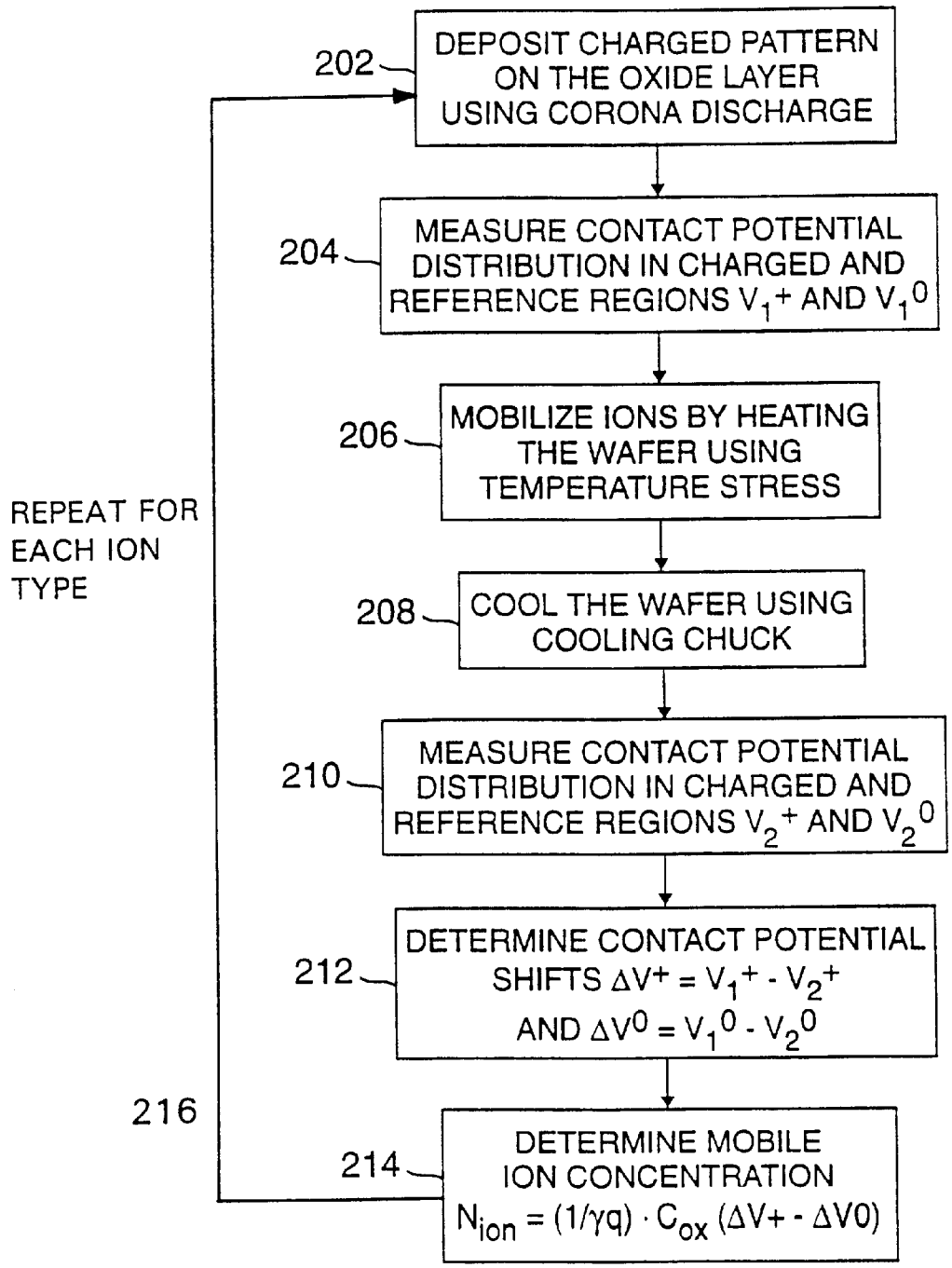
FIG. 9 is a flow diagram of a technique for measuring the mobile ion concentration in accordance with the invention.

Referring as well to FIG. 9, a flow chart illustrates an automated approach having relatively few steps and, therefore, offers a relatively fast determination of different mobile ion concentrations with a basic measuring sequence corresponding to that of FIGS. 6A–6C. Robotic handler 12 picks up a silicon wafer 6 having a SiO$_2$ layer 4 from the cassette holder 14. Handler 12 moves wafer 6 to a prealigner 16. After prealigning, wafer 6 is transported by robotic handler 12 to the wafer chuck 32 of the corona charging station 30. Rotation of wafer 6 is activated by motor 36 and a high DC positive voltage is applied to the corona discharge wire 42 for a predetermined period of time.

Figure 10:
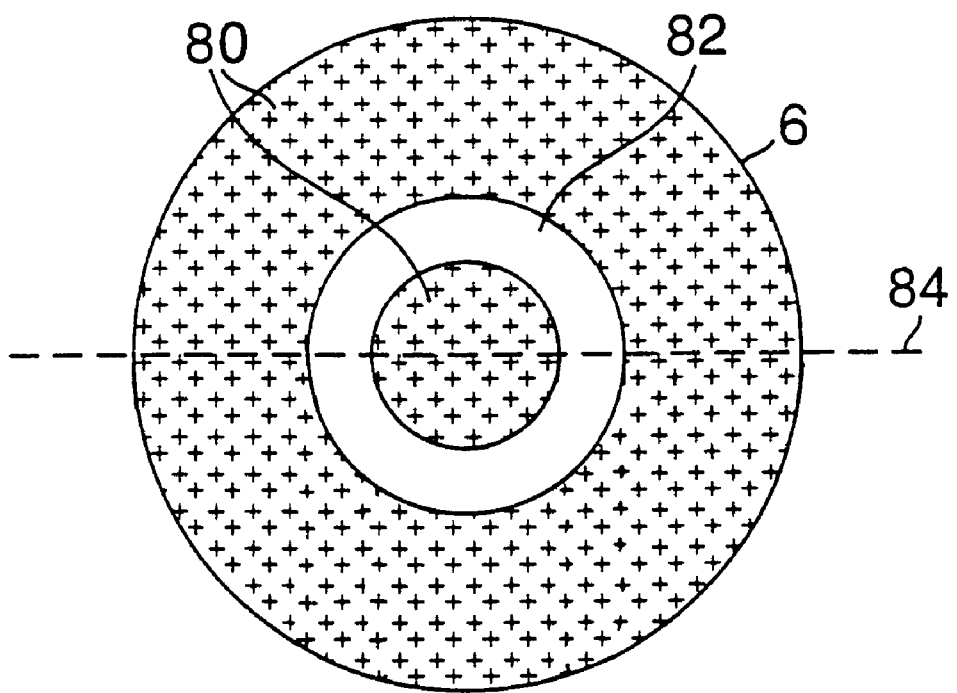
FIG. 10 is a top view of the semiconductor wafer showing regions of deposited charge.

A predetermined corona charge, e.g., 0.5 MV/cm$^2$, is deposited on the top surface of the oxide in a pattern, shown in FIG. 10, containing charged regions 80, and reference region 82 (step 202). Wafer 6 is then transported by robot 12 to a measuring station 20 and the contact potential distribution is measured (with measuring device 22) in the form of a line scan across the wafer diameter giving the values of $V_1^+$ and $V_1^0$ in the charged and reference regions, respectively (step 204). Silicon wafer 6 is then moved by robotic handler 12 to temperature stress station 90. It is placed on the heated chuck and held at a predetermined temperature of e.g., 175° C. (to enhance the mobility of the ions) for a predetermined time period e.g., approximately four minutes (step 206). As discussed above, the predetermined amounts of corona charge, temperature, and heating time are selected to force selectively different ions to migrate within the oxide layer. The first set of mobile, positive ions are repelled by the positive corona charge and drift toward the oxide/semiconductor interface (as shown in FIG. 6C). Wafer 6 is placed by robotic handler 12 on the cooling chuck and is cooled e.g., to room temperature (step 208). The wafer is then transported to measuring station 20 and contact potential distribution is measured with measuring device 22 (Step 210) in the same manner as in step 204, giving the corresponding values $V_2^+$ and $V_2^0$ in the charged and reference regions, respectively. The difference between $V_1^+$ and $V_2^+$ provides the contact potential shift $\Delta V^+$ and the difference between $V_2^0$ and $V_2^0$ provides the reference contact potential shift $\Delta V^0$ (step 212) both of which are used in calculations to determine the first mobile ion concentration (step 214). The calculation of the first mobile ion concentration (Step 214) involves the coefficient γ which depends on the ion distribution. If during the $V_1^+$ measurement (Step 204, prior to temperature stress) the ions are located at the top of the oxide surface and after temperature stress they are at silicon/$SiO_2$ interface, then γ=1. If the ions were initially distributed in a uniform manner across the oxide thickness, γ=0.5. Discussion of γ is given in D. K. Schroder "Semiconductor Material and Device Characterization", John Wiley & Sons, Inc., 1990, Ch. 6, p. 253, the entire contents of which is incorporated herein by reference. Robot handler 12 moves wafer 6 back to corona charging station 30 (Step 216) and system 10 repeats steps 202–214 for each type of ion.

The uncertainty in the γ value can be improved by adding a pre-BTS conditioning step before executing the sequence shown in FIG. 9. The pre-BTS conditioning step forces all of the ions to migrate away from the interface towards the top surface of the oxide layer (FIG. 8A). Once preconditioned, γ is approximately 1 for each ion type. Pre-BTS conditioning is performed. Handler 12 moves a wafer onto charging station 30 and a preselected amount of negative corona charge, e.g., −1.5 MV/cm², is deposited on the oxide surface (FIG. 8A). Handle 12 moves the wafer to temperature stress station 90 and a predetermined amount of heat, e.g., 175° C., is applied to the wafer for a predetermined time. The pre-BTS conditions, typically, are determined via equations 7 and 8 and by assuming that the least mobile ion type needs to migrate −$d_{ox}$. Once the pre-BTS conditioning is complete, the wafer is cooled, and transported back to charging station 30. During the first cycle of the measurement sequence described in FIG. 9, the predetermined amount of positive corona charge deposited on the oxide layer is increased to cancel the negative charge deposited during the pre-BTS conditioning. The remaining cycles of measuring different ion types are the same as described above in FIG. 9.

The accuracy of the measurement can be further improved by measuring the change in contact voltage due to ion migration from the interface towards the oxide surface. Once all ion types are forced to the interface, system 10 may selectively force different ion types to the oxide surface by applying predetermined amounts of negative corona charge and subsequently applying predetermined heating for a predetermined time. Further accuracy can be obtained by complimenting all contact potential measurement steps (e.g., Steps 204, 210, 224, and 230) with corresponding SPV measurements of the surface potential barrier, $V_s$ (as shown in FIGS. 5–7). These measurements are performed by measuring device 24 while wafer 6 is still on the measuring stage, immediately following contact potential measurement of a positive corona charge. For example, these additional steps would be given the surface barrier value $V_{s1}^+$ in the charged region and $V_{s1}^0$ in the reference region, and $V_{s2}^+$ and $V_{s2}^0$ for the charged and the reference regions, respectively. In the ideal case of no significant ion neutralization or charge injection into oxide during corona temperature stress, there is no significant surface barrier shift ($\leq$10 mV for 100 Å oxide or $\leq$100 mV for 1000 Å oxide). In this case, the surface barrier measurement confirms the validity of the approach and no corrections are needed in determining the mobile ion concentration. If surface barrier shifts are larger than 10 mV for thin oxides or 100 mV for thicker oxides, the corresponding corrections are introduced by subtracting surface barrier value shifts from the contact potential shifts.

Thus, the formula in Step 214 is replaced by:

$$N^i_{ion}=(1/\gamma q)C_{ox}(\Delta V^+-\Delta V_s^+-\Delta V^0+\Delta V_s^0)$$

where: $\Delta V_s^+=V_{s1}^+-V_{s2}^+$ and $\Delta V_s^0=\Delta V_{s1}^0-\Delta V_{s2}^0$.

The uncertainty of the approach increases when the surface barrier shifts are very large. This may be especially important for thin oxides and low mobile ion concentration when contact potential shifts associated with ion drifts are only a fraction of one volt. If the surface barrier shifts are comparable to or larger than contact potential shifts, the approach may be considered invalid due to a dominant role of interfering effects. Still further accuracy in determining the concentration of different ion type is obtained by correcting the change in contact potential for oxide leakage, which could reduce corona charge. Presence of leakage causes the contact potential to decrease over time and depending on the magnitude of leakage may introduce errors into the measured contact potentials and thereby result in inflated values of ion concentration. Leakage error can be corrected after all the ions have migrated either towards the interface or the top surface of the oxide. In either case, system 10 sequentially reapplies each BTS-condition used to force substantially or preferably all different ion types to the interface or top surface and measures the contact potential after each predetermined corona charging, $V^+_{1\text{-}LEAK}$, as well as after each predetermined heating and time period, $V^+_{2\text{-}LEAK}$. Since all of the ions are either at the interface or surface, they cannot migrate and do not contribute to the measured contact potential. As a result, differences in the contact potential, $\Delta V^+_{LEAK}$, i.e., $V^+_{1\text{-}LEAK}-V^+_{2\text{-}LEAK}$, are due to leakage.

Accordingly, $\Delta V^+_{LEAK}$ can be used to correct the calculated concentration of each ion. The formula in Step 214 is replaced by:

$$N^i_{ion}=(1/\gamma q)C_{ox}(\Delta V^+-V_{LEAK}^+)$$

EXAMPLE

SIMS measurements (not shown) demonstrated that BTS-conditioning at about 170° C. for about 2 minutes at about ±0.5 MV/cm causes $Na^+$ present within a 1000 Å thick oxide layer to migrate to the $SiO_2$/Si interface, but does not affect the migration of $Cu^+$ ions at the oxide surface (due to orders of magnitude lower Cu mobility).

Figure 11:
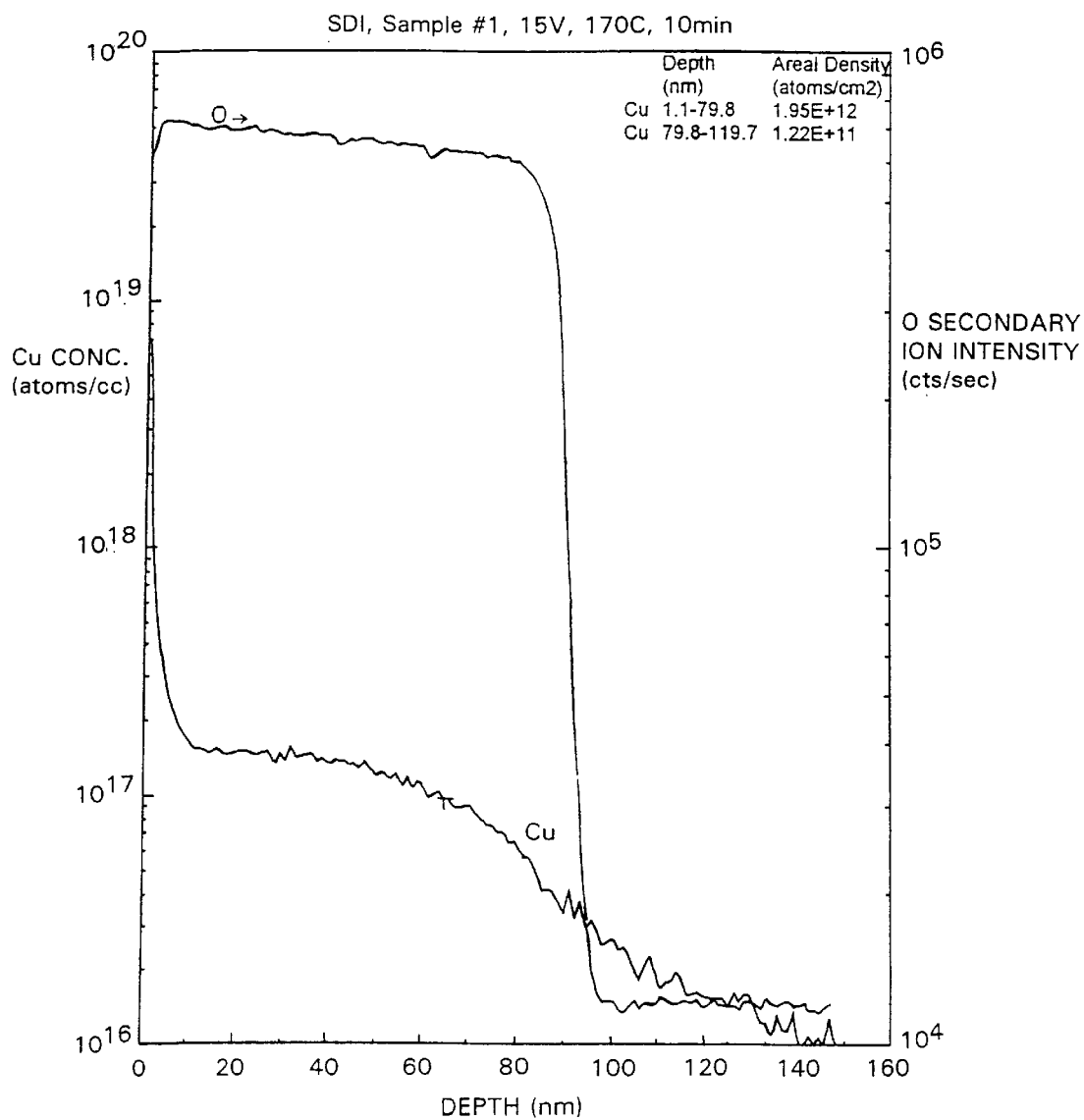
FIGS. 11–13 are spectra of secondary-ion mass spectroscopic experiments.
Figure 12:
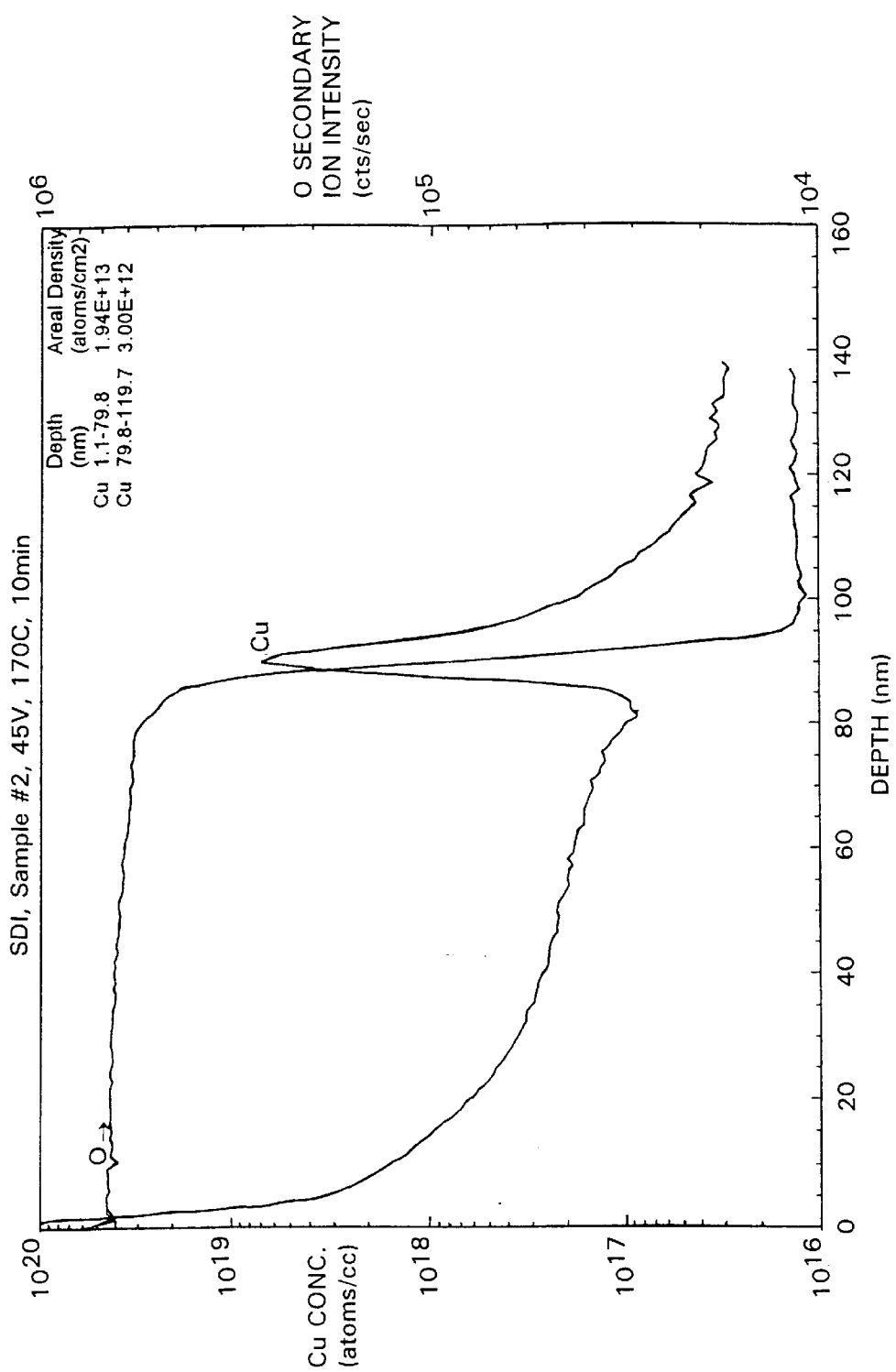

SIMS measurements of $Cu^+$ in the oxide after different BTS conditions (FIGS. 11 to 13) also demonstrated that during 1.5 MV/cm, 170° C., 10 min BTS-conditioning, $Cu^+$ did not transfer across entire 1000 Å of oxide thickness, i.e., the $Cu^+$ concentration dropped below E17 $cm^{-3}$ after distance of about 600 Å, and no $Cu^+$ accumulation on the Si/$SiO_2$ interface was detected (FIG. 11). At 3 times higher electric field of 4.5 MV/cm (for same temperature and time) $Cu^+$ migrated through the entire 1000 Å thickness and accumulated at the interface (FIG. 12). Since transfer distance is proportional to electric field and time, it will take about 30 minutes to transfer $Cu^+$ through 1000 Å thick oxide at 1.5 MV/cm field and at 170° C.

Figure 13:
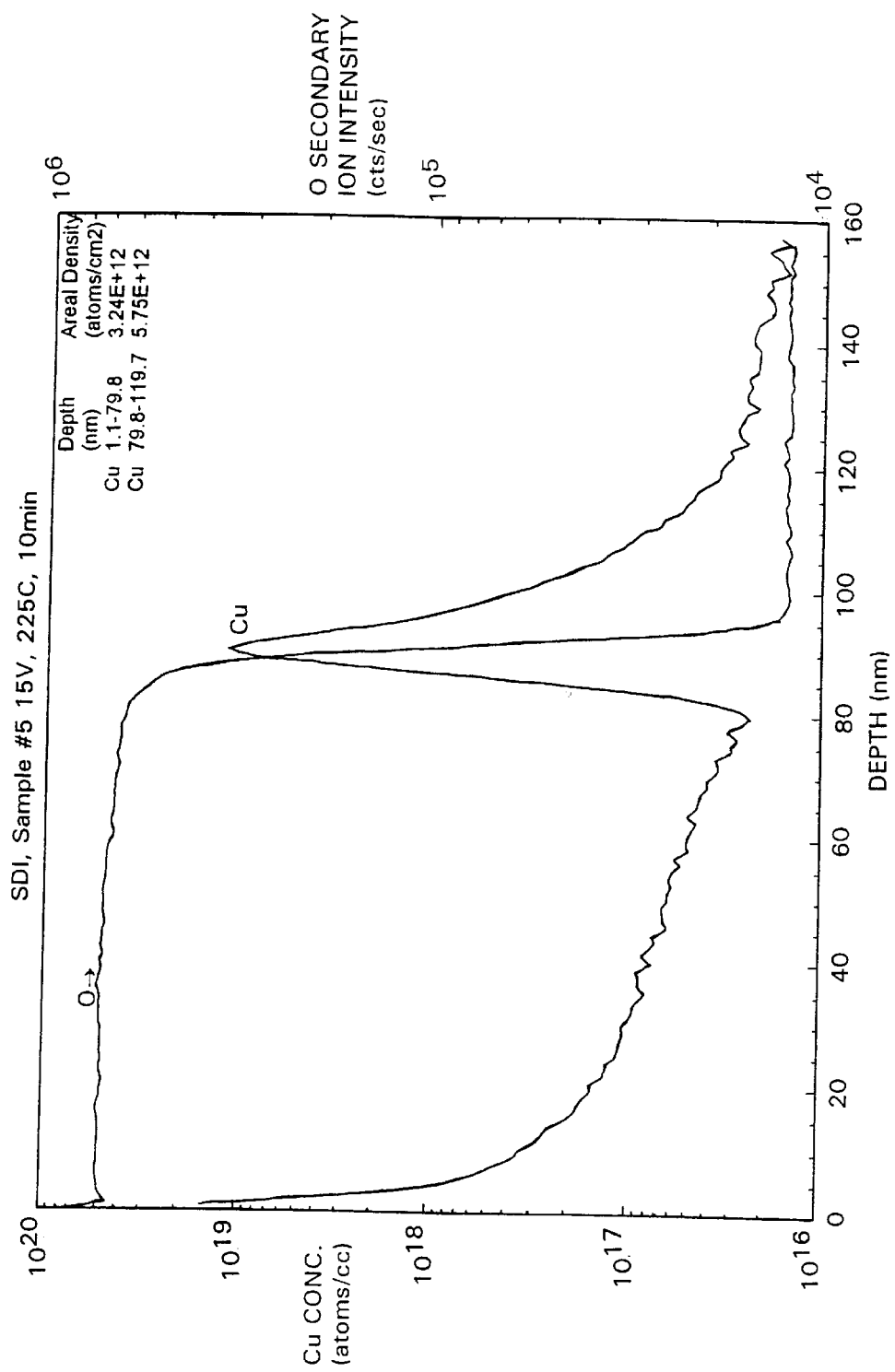

BTS-conditioning of 225° C. for 10 minutes at 1.5 MV/cm resulted in migration of 2 times larger amount of $Cu^+$ through the oxide than for the BTS-conditioning of 170° C. for 10 minutes at 4.5 MV/cm (compare $Cu^+$ concentration accumulated at the interface FIGS. 12 and 13). For a 4.5 MV/cm field, increasing the temperature from 170° C. to 225° C. results in an increase in the $Cu^+$ transfer rate of about 6 times. Since $Cu^+$ transfer through 1000 Å of oxide requires BTS-conditioning of about 170° C. for about 30 minutes at about 1.5 MV/cm, only about 5 minutes of BTS-conditioning are required at about 225° C. and about 1.5 MV/cm.

Other embodiments are within the appended claims.

What is claimed is:

1. A method of measuring at least two different ion concentrations within an oxide layer of a semiconductor, the method comprising:

applying a first predetermined bias temperature stress (BTS)-conditioning to the semiconductor wafer including the oxide layer disposed thereon to cause ions of a first type to migrate within the oxide layer; and applying a second predetermined BTS-conditioning to the semiconductor wafer to cause ions of a second type to migrate within the oxide layer, wherein the first predetermined BTS-conditioning does not substantially cause the ions of the second type to migrate within the oxide layer.

2. The method of claim 1 further including measuring the first contact potential after the ions of the first type migrate within the oxide layer.

3. The method of claim 2 wherein the first contact potential is also measured before the ions of the first type migrate within the oxide layer.

4. The method of claim 2 further including measuring the second contact potential after the ions of the second type migrate within the oxide layer.

5. The method of claim 4, wherein the second contact potential is also measured before the ions of the second type migrate within the oxide layer.

6. The method of claim 4 including measuring the oxide leakage current at the first and the second predetermined BTS-conditionings, correcting the first contact potential with the oxide leakage current measured at the first predetermined BTS-conditioning, and correcting the second contact potential with the oxide leakage current measured at the second predetermined BTS-conditioning.

7. The method of claim 1 further including measuring the second contact potential after the ions of the second type migrate within the oxide layer.

8. The method of claim 7 the second contact potential is also measured before the ions of the second type migrate within the oxide layer.

9. The method of claim 1, wherein the first predetermined BTS-conditioning includes biasing the semiconductor wafer with a predetermined first charge and heating the semiconductor wafer to a predetermined first temperature for a predetermined first time period.

10. The method of claim 1, wherein the second predetermined BTS-conditioning includes biasing the semiconductor with a predetermined second charge and heating the semiconductor wafer to a predetermined second temperature for a predetermined second time period.

11. The method of claim 1 further including a pre-BTS conditioning to cause a random distribution of ions of the first and second types to redistribute into a non-random distribution.

12. The method of claim 11, wherein the ions of the first and second types are caused to migrate to the surface of the oxide layer.

13. The method of claim 11, wherein the ions of the first and second types are caused to migrate to an interface between the oxide layer and the semiconductor.

14. The method of claim 1, wherein the ions of the first type have an ion mobility that is larger than the ion mobility of the ions of the second type at a constant temperature.

15. The method of claim 1, wherein the ions of the first type are $Na_+$.

16. The method of claim 15, wherein the ions of the second type are $Cu^+$.

17. The method of claim 1, wherein the semiconductor wafer further includes a metal layer periodically patterned on a top surface of the oxide layer.

18. The method of claim 17, wherein the metal layer is copper.

19. The method of claim 1, wherein the first predetermined BTS-conditioning includes biasing the semiconductor with a predetermined first charge and heating the semiconductor wafer to a predetermined first temperature for a predetermined first time period, and the second predetermined BTS-conditioning includes biasing the semiconductor with a predetermined second charge and heating the semiconductor wafer to a predetermined second temperature for a predetermined second time period.

20. The method of claim 19, wherein the first charge and the second charge are equal.

21. The method of claim 20, wherein the first temperature and the second temperature are equal.

22. The method of claim 20, wherein the first time period and a second time period are equal.

23. The method of claim 19, wherein the first temperature and the second temperature are equal.

24. The method of claim 23, wherein the first time period and a second time period are equal.

25. The method of claim 19, wherein the first time period and a second time period are equal.

26. The method of claim 19, wherein the first and the second temperatures are between about 150° C. and about 300° C.

27. The method of claim 19, wherein the first and the second charges are between about 0.1 to about 6 MV/cm.

28. The method of claim 19, wherein the first and the second time periods are between 30 sec and 3600 sec.

29. The method of claim 19, wherein the second predetermined BTS-conditioning includes biasing the semiconductor with a charge of about 1.5 MV/cm and heating the semiconductor to about 170° C. for a time period of at least about 20 minutes for a 1000 Å oxide thickness.

30. The method of claim 29, wherein first predetermined BTS-conditioning includes biasing the semiconductor with a charge of about 0.5 MV/cm and heating the semiconductor to about 170° C. for a time period of at least about 2 minutes for a 1000 Å oxide thickness.

31. The method of claim 19, wherein the second predetermined BTS-conditioning includes biasing the semiconductor with a charge of about 1.5 MV/cm and heating the semiconductor to about 2250° C. for a time period of at least about 3.5 minutes for a 1000 Å oxide thickness.

32. The method of claim 19, wherein the biasing charges applied to the surface of the oxide layer are produced from a corona charging element.

33. A method for determining different mobile ion concentrations within an oxide layer disposed on a surface of a semiconductor wafer, comprising:

depositing a first charge on at least a portion of the surface of the oxide layer at a low temperature at which a first mobile ion does not substantially move, measuring the contact potential on the surface of the oxide layer, heating the semiconductor wafer and oxide layer to a first temperature sufficient to force substantially all of the first mobile ions to migrate across the oxide layer from the surface to an interface between the oxide layer and semiconductor wafer, measuring a first shift in contact potential after said heating to the first temperature, determining the first mobile ion concentration within the oxide layer on the basis of the first shift;

depositing a second charge on at least a portion of the surface of the oxide layer at a low temperature at which a second mobile ion does not substantially move, measuring the contact potential on the surface of the oxide layer, heating the semiconductor wafer and oxide layer to a second temperature sufficient to force substantially all of the second mobile ions to migrate within the oxide layer from the surface to an interface between the oxide layer and semiconductor wafer, measuring a second shift in contact potential after said heating to the second temperature, determining the second mobile ion concentration within the oxide layer on the basis of the second shift.

34. The method of claim 33 further including determining the oxide leakage at the first charge and the second charge and using the oxide leakage at the first charge and the second charge in determining the first and second ion concentrations.

35. A system for the measurement of mobile contaminant ion concentration in an oxide layer of a semiconductor wafer, comprising:

a charge deposition device configured to deposit charge on the oxide layer of the wafer;

a temperature stress device including a element for heating the wafer to a temperature sufficient to allow mobile ions to drift;

a measurement device configured to measure the contact potential; and a semiconductor wafer holder including at least one semiconducting wafer having an oxide layer disposed on a surface of a semiconductor wafer, wherein a metal layer is patterned onto a surface of the oxide layer.

* * * * *